(12) United States Patent
Aoyagi et al.

(10) Patent No.: US 7,316,905 B1
(45) Date of Patent: *Jan. 8, 2008

(54) METHOD FOR MEASUREMENT OF HEPATITIS C VIRUS

(75) Inventors: Katsumi Aoyagi, Wako (JP); Chiharu Ohue, Wako (JP); Kumiko Iida, Wako (JP); Shintaro Yagi, Wako (JP)

(73) Assignee: Advanced Life Science Institute, Inc., Saitama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/509,449

(22) PCT Filed: Jul. 30, 1999

(86) PCT No.: PCT/JP99/04129

§ 371 (c)(1),
(2), (4) Date: Mar. 28, 2000

(87) PCT Pub. No.: WO00/07023

PCT Pub. Date: Feb. 10, 2000

(30) Foreign Application Priority Data

Jul. 30, 1998   (JP) ................................ 10-216094

(51) Int. Cl.
| | |
|---|---|
| G01N 33/53 | (2006.01) |
| G01N 33/569 | (2006.01) |
| C12Q 1/70 | (2006.01) |
| C12Q 1/00 | (2006.01) |
| C07K 2/00 | (2006.01) |
| C07K 14/00 | (2006.01) |
| C07K 14/08 | (2006.01) |
| C07K 16/00 | (2006.01) |
| C07K 16/08 | (2006.01) |
| C07K 16/10 | (2006.01) |

(52) U.S. Cl. ................ 435/7.1; 435/4; 435/5; 435/7.92; 435/8; 530/300; 530/350; 530/387.1; 530/387.9

(58) Field of Classification Search .......... 435/4, 435/5, 7.1, 7.9, 7.92, 7.93, 7.94, 7.95, 287.1, 435/287.2, 287.9; 530/300, 324, 325, 326, 530/328, 350, 387.1, 388.1, 388.2, 388.3, 530/391.1, 403; 436/506, 507, 512, 513, 436/518, 536, 820

See application file for complete search history.

(56) References Cited

U.S. PATENT DOCUMENTS

| 4,148,869 A | | 4/1979 | Deaton |
|---|---|---|---|
| 4,639,425 A | * | 1/1987 | Baier ......................... 436/518 |
| 4,668,639 A | * | 5/1987 | Johannsson ................ 436/518 |
| 5,032,503 A | * | 7/1991 | Khanna et al. .............. 435/7.6 |
| 5,330,893 A | | 7/1994 | Gilbert et al. |
| 5,616,460 A | | 4/1997 | Figard |
| 5,627,026 A | * | 5/1997 | O'Connor et al. ............. 435/5 |
| 5,627,080 A | * | 5/1997 | Cheng et al. ................ 436/534 |
| 5,645,983 A | | 7/1997 | Liao et al. |
| 5,811,525 A | * | 9/1998 | Rittershaus ............ 530/388.22 |
| 5,843,450 A | * | 12/1998 | Dawson et al. .......... 424/189.1 |
| 6,183,949 B1 | * | 2/2001 | Seidel et al. .................... 435/5 |

FOREIGN PATENT DOCUMENTS

| EP | 0 173 295 | | 3/1986 |
|---|---|---|---|
| EP | 0 351 248 | | 1/1990 |
| EP | 0 507 615 | * | 4/1992 |
| EP | 0 967 484 | | 12/1999 |
| GB | 2313666 | * | 1/1981 |
| GB | WO 93/10239 | * | 5/1993 |
| GB | 2051357 | * | 3/1997 |
| JP | 60-4938 | | 2/1985 |
| JP | 60-24451 A | | 2/1985 |
| JP | 64-15656 | | 1/1989 |
| JP | 06-38765 | | 2/1994 |
| JP | 6-300761 | | 10/1994 |
| JP | 8-5633 A | | 1/1996 |
| JP | 8-50133 | | 2/1996 |
| JP | 11-108932 | | 4/1999 |
| WO | 93/21346 | | 10/1993 |
| WO | WO99/06836 | * | 2/1999 |

OTHER PUBLICATIONS

Masalova et al., Detection of hepatitis C virus core protein circulating within different virus particle populations. Journal of Medical Virology 55(1):1-6, May 1998.*
Aoyagi et al., Development of a Simple and Highly Sensitive Enzyme Immunoassay for Hepatitis C Virus Core Antigen. Journal of Clinical Microbiology 37(6): 1802-1808, Jun. 1999.*
Papatheodoridis et al., Journal of Hepatology, vol. 27, pp. 36-41 (1997).*
Ferroni et al. Journal of CLinical Microbiology, vol. 31 No. 6, pp. 1586-1591 (Jun. 1993).*
International Search Report dated Oct. 4, 1999, prepared by JPO.
Higa. "Calcium-dependent Bacteriophage DNA Infection," *Letters to the Editor, Journal of Molecular Biology*, vol. 53 (1970): pp. 159-162.
Kohler et al. "Continuous cultures of fused cells secreting antibody of predefined specificity,"*Nature*, vol. 256 (Aug. 7, 1975): pp. 495-497.
Kohler et al. "Derivation of specific antibody-producing tissue culture and tumor lines by cell fusion," *European Journal of Immunology*, vol. 6 (1976): pp. 511-519.
Chiba et al. "Serodiagnosis hepatitis C virus (HCV) infection with an HCV core protein molecularly expressed by a recombinant baculovirus," *Proc. National Academy of Science*, vol. 88 (Jun. 1991): pp. 4641-4645.

(Continued)

*Primary Examiner*—Zachariah Lucas
(74) *Attorney, Agent, or Firm*—Merchant & Gould P.C.

(57) ABSTRACT

A method for measurement of the hepatitis C virus (HCV) characterized by measuring HCV core antigen and HCV core antibody by their binding with probes in the presence of an anionic surfactant or a non-ionic surfactant, or both.

2 Claims, 2 Drawing Sheets

OTHER PUBLICATIONS

Takahashi et al. "Demonstration of a hepatitis C virus-specific antigen predicted from the putative core gene in the circulation of infected hosts," *Journal of General Virology*, vol. 73 (1992): pp. 667-672.

Sang. *Enhanced Sensitivity of a Second Generation ELISA for Antibody to Hepatitis C Virus*. 1992, pp. 213-217.

Okamoto et al. "Antibodies Against Synthetic Oligopeptides Deduced from the Putative Core Gene for the Diagnosis of Hepatitis C Virus Infection," *Hepatology*, vol. 15, No. 2 (1992): pp. 180-186.

Sallberg et al. "Immunodominant Regions within the Hepatitis C Virus Core and Putative Matrix Proteins," *Journal of Clinical Microbiology*, vol. 30, No. 8 (Aug. 1992): pp. 1989-1994.

Machida et al. "Two Distinct Subtypes of hepatitis C Virus Defined by Antibodies Directed to the Putative Core Protein," *Hepatology*, vol. 16, No. 4 (1992): pp. 886-891.

Sallberg et al. "Locations of Antibody Binding Sites within Conserved Regions of the Hepatitis C Virus Core Protein," *Journal of Medical Virology*, vol. 43 (1994): pp. 62-68.

Kashiwakuma et al. "Detection of hepatitis C virus specific core protein in serum of patients by a sensitive fluorescence enzyme immunoassay (FEIA)", *Journal of Immunological Methods*, vol. 190 (1996): pp. 79-89.

Hoogenboom. "Designing and optimizing library selection strategies for generating high-affinity antibodies," *Tibtech*, vol. 15 (Feb. 1997): pp. 62-70.

Weber et al. "Reduction of Diagnostic Window by New Fourth-Generation Human Immunodeficiency Virus Screening Assays," *Journal of Clinical Microbiology*, vol. 36, No. 8 (Aug. 1998): pp. 2235-2239.

Kashiwakuma, et al., Detection of hepatitis C virus specific core protein in serum of patients by a sensitive fluorescence enzyme immunoassay (FEIA), Journal of Immunological Methods 190 (1996) 79-89.

Atherton, et al., "A sensitive Screening Test for the Simultaneous Detectionof Hepatitis B Surface Antigen and Antibody", Journal of Virological Methods 13 (1986) 245-253.

Van Der Poel, Cees L., "Hepatitis C virus: Into the fourth generation", VOX SANGUINIS, vol. 67, No. suppl. 3, 1994, pp. 95-98.

Fonseca, et al., "Comparison of reactivity of sera tested in a third generation enzyme immunoassay (EIA) and recombinant immunoblot (RIBA) versus fourth generation EIA for antibody to hepatitis C virus (HCV)", 96h ASM General Meeting, 1996.

* cited by examiner

SEQUENCE LISTING

<160> NUMBER OF SEQ ID NOS: 11

<210> SEQ ID NO 1
<211> LENGTH: 177
<212> TYPE: PRT
<213> ORGANISM: Hepatitis C virus

<400> SEQUENCE: 1

Met Lys Ala Ile Phe Val Leu Lys Gly Ser Leu Asp Arg Asp Pro Glu
1               5                   10                  15

Phe Met Gly Thr Asn Pro Lys Pro Gln Arg Lys Thr Lys Arg Asn Thr
            20                  25                  30

Asn Arg Arg Pro Gln Asp Val Lys Phe Pro Gly Gly Gly Gln Ile Val
        35                  40                  45

Gly Gly Val Tyr Leu Leu Pro Arg Arg Gly Pro Arg Leu Gly Val Arg
    50                  55                  60

Ala Thr Arg Lys Thr Ser Lys Arg Ser Gln Pro Arg Gly Gly Arg Arg
65                  70                  75                  80

Pro Ile Pro Lys Asp Arg Arg Ser Thr Gly Lys Ser Trp Gly Lys Pro
                85                  90                  95

Gly Tyr Pro Trp Pro Leu Tyr Gly Asn Glu Gly Leu Gly Trp Ala Gly
            100                 105                 110

Trp Leu Leu Ser Pro Arg Gly Ser Arg Pro Ser Trp Gly Pro Thr Asp
        115                 120                 125

Pro Arg His Arg Ser Arg Asn Val Gly Lys Val Ile Asp Thr Leu Thr
    130                 135                 140

Cys Gly Phe Ala Asp Leu Met Gly Tyr Ile Phe Arg Val Gly Ala Phe
145                 150                 155                 160

Leu Gly Gly Ala Ala Arg Ala Leu Ala His Gly Val Arg Val Leu Glu
                165                 170                 175

Asp

<210> SEQ ID NO 2
<211> LENGTH: 160
<212> TYPE: PRT
<213> ORGANISM: Hepatitis C virus

<400> SEQUENCE: 2

Met Gly Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Lys Arg Ser Gln Pro Arg Gly Gly Arg Arg Pro

```
                50                  55                  60
Ile Pro Lys Asp Arg Arg Ser Thr Gly Lys Ser Trp Gly Lys Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg His Arg Ser Arg Asn Val Gly Lys Val Ile Asp Thr Leu Thr Cys
                115                 120                 125

Gly Phe Ala Asp Leu Met Gly Tyr Ile Phe Arg Val Gly Ala Phe Leu
                130                 135                 140

Gly Gly Ala Ala Arg Ala Leu Ala His Gly Val Arg Val Leu Glu Asp
145                 150                 155                 160

<210> SEQ ID NO 3
<211> LENGTH: 20
<212> TYPE: PRT
<213> ORGANISM: Artificial Sequence
<220> FEATURE:
<223> OTHER INFORMATION: Fused polypeptide including Hepatitis C virus
      sequence.

<400> SEQUENCE: 3

Asp Val Lys Phe Pro Gly Gly Gly Gln Ile Val Gly Gly Val Tyr Leu
1               5                   10                  15

Leu Pro Arg Arg
            20

<210> SEQ ID NO 4
<211> LENGTH: 10
<212> TYPE: PRT
<213> ORGANISM: Artificial Sequence
<220> FEATURE:
<223> OTHER INFORMATION: Fused polypeptide including Hepatitis C virus
      sequence.

<400> SEQUENCE: 4

Gly Pro Arg Leu Gly Val Arg Ala Thr Arg
1               5                   10

<210> SEQ ID NO 5
<211> LENGTH: 21
<212> TYPE: PRT
<213> ORGANISM: Artificial Sequence
<220> FEATURE:
<223> OTHER INFORMATION: Fused polypeptide including Hepatitis C virus
      sequence.

<400> SEQUENCE: 5

Pro Arg Gly Ser Arg Pro Ser Trp Gly Pro Thr Asp Pro Arg His Arg
1               5                   10                  15

Ser Arg Asn Val Gly
            20

<210> SEQ ID NO 6
<211> LENGTH: 20
<212> TYPE: PRT
<213> ORGANISM: Artificial Sequence
<220> FEATURE:
<223> OTHER INFORMATION: Fused polypeptide including Hepatitis C virus
      sequence.

<400> SEQUENCE: 6
```

```
Asp Pro Arg His Arg Ser Arg Asn Val Gly Lys Val Ile Asp Thr Leu
1               5                   10                  15

Thr Cys Gly Phe
            20

<210> SEQ ID NO 7
<211> LENGTH: 24
<212> TYPE: DNA
<213> ORGANISM: Artificial Sequence
<220> FEATURE:
<223> OTHER INFORMATION: Primer for polymerase chain reaction.

<400> SEQUENCE: 7
gaattcatgg gcacgaatcc taaa                                           24

<210> SEQ ID NO 8
<211> LENGTH: 21
<212> TYPE: DNA
<213> ORGANISM: Artificial Sequence
<220> FEATURE:
<223> OTHER INFORMATION: Primer for polymerase chain reaction.

<400> SEQUENCE: 8
ttagtcctcc agaacccgga c                                              21

<210> SEQ ID NO 9
<211> LENGTH: 16
<212> TYPE: PRT
<213> ORGANISM: Artificial Sequence
<220> FEATURE:
<223> OTHER INFORMATION: Portion of Hepatitis C virus sequence.

<400> SEQUENCE: 9

Thr Asn Arg Arg Pro Gln Asp Val Lys Phe Pro Gly Gly Gly Gln Ile
1               5                   10                  15

<210> SEQ ID NO 10
<211> LENGTH: 1197
<212> TYPE: DNA
<213> ORGANISM: Artificial Sequence
<220> FEATURE:
<223> OTHER INFORMATION: Nucleotide sequence coding for chimeric
      antigen.
<221> NAME/KEY: CDS
<222> LOCATION: (1)..(1188)
<223> OTHER INFORMATION:

<400> SEQUENCE: 10 gaa ttc acc aaa gtg ccg gtt gct tat gcg gcc aaa ggt tat aag gtc    48
Glu Phe Thr Lys Val Pro Val Ala Tyr Ala Ala Lys Gly Tyr Lys Val
1               5                   10                  15 ctg gtt ctg gac ccg agc gtt gcc agc acc ctg ggt ttc ggc gcg tat    96
Leu Val Leu Asp Pro Ser Val Ala Ser Thr Leu Gly Phe Gly Ala Tyr
            20                  25                  30 ctg agc aag gcc cat ggt gtg aac ccg aac atc cgc acg ggc atc cgt   144
Leu Ser Lys Ala His Gly Val Asn Pro Asn Ile Arg Thr Gly Ile Arg
        35                  40                  45 acc gtt acc acc ggt gct ccg gtg acc tat tcc acc tac ggt aaa tac   192
Thr Val Thr Thr Gly Ala Pro Val Thr Tyr Ser Thr Tyr Gly Lys Tyr
    50                  55                  60 ctg gcg gac ggc ggt tgc gcc ggc ggt gcg tac gat gtg atc gga tct   240
Leu Ala Asp Gly Gly Cys Ala Gly Gly Ala Tyr Asp Val Ile Gly Ser
65                  70                  75                  80 gga gag gag gtg gcc ctg tct aac act gga gag gtc ccc ttc tat ggc   288
Gly Glu Glu Val Ala Leu Ser Asn Thr Gly Glu Val Pro Phe Tyr Gly
```

|  |  |
|---|---|
| cgc gcg atc ccg atc gaa gcg atc aaa ggc ggt cgc cat ctg gtt ttc<br>Arg Ala Ile Pro Ile Glu Ala Ile Lys Gly Gly Arg His Leu Val Phe<br>                    100                    105                  110 | 336 |
| tgc cat agc aag gag aaa tgc gat gaa ctg gcg agc gcg ctg tcc gga<br>Cys His Ser Lys Glu Lys Cys Asp Glu Leu Ala Ser Ala Leu Ser Gly<br>        115                    120                    125 | 384 |
| ttg ggt ctg aac gct gtg gca ttc tat cgc ggt ctg gac gtg agc att<br>Leu Gly Leu Asn Ala Val Ala Phe Tyr Arg Gly Leu Asp Val Ser Ile<br>130                    135                    140 | 432 |
| atc ccg acc cag ggc gat gtg gtt atc gtt agc acc gat gcg ctg atg<br>Ile Pro Thr Gln Gly Asp Val Val Ile Val Ser Thr Asp Ala Leu Met<br>145                    150                    155                    160 | 480 |
| acc ggt ttt acc ggc gat ttt gac tca gtg gtc gac tgt aac aca tgc<br>Thr Gly Phe Thr Gly Asp Phe Asp Ser Val Val Asp Cys Asn Thr Cys<br>                    165                    170                    175 | 528 |
| atc acc cag gga tct gga ctg gta agc ttc gcg agc cat gtg ccg tac<br>Ile Thr Gln Gly Ser Gly Leu Val Ser Phe Ala Ser His Val Pro Tyr<br>        180                    185                    190 | 576 |
| atc gag cag ggt atg caa ctg agc gaa caa ttt aag cag aag agc ctg<br>Ile Glu Gln Gly Met Gln Leu Ser Glu Gln Phe Lys Gln Lys Ser Leu<br>                    195                    200                    205 | 624 |
| ggt ctg ctg cag acc gcg acc aaa cag gcg gag gcg gcc gcc ccg gtg<br>Gly Leu Leu Gln Thr Ala Thr Lys Gln Ala Glu Ala Ala Ala Pro Val<br>210                    215                    220 | 672 |
| gtt ggc acc ccg aaa agc cgc cgt ccg gaa ggt cgt gcc tgg gcg caa<br>Val Gly Thr Pro Lys Ser Arg Arg Pro Glu Gly Arg Ala Trp Ala Gln<br>225                    230                    235                    240 | 720 |
| ccg ggt acc atc atc ctg agc ggt cgt ccg gcg gtt gta ccg gat cgt<br>Pro Gly Thr Ile Ile Leu Ser Gly Arg Pro Ala Val Val Pro Asp Arg<br>                    245                    250                    255 | 768 |
| gaa gtg ctg tat caa gaa ttt ctc gag gcc tct aga gcg gct ctc att<br>Glu Val Leu Tyr Gln Glu Phe Leu Glu Ala Ser Arg Ala Ala Leu Ile<br>        260                    265                    270 | 816 |
| gaa gag ggg caa cgg ata gcc gag atg ctg aag tcc aag atc cag ggc<br>Glu Glu Gly Gln Arg Ile Ala Glu Met Leu Lys Ser Lys Ile Gln Gly<br>                    275                    280                    285 | 864 |
| tta ctg cag caa gcc tcc aag cag gcc caa gac ata aaa atc gac ggt<br>Leu Leu Gln Gln Ala Ser Lys Gln Ala Gln Asp Ile Lys Ile Asp Gly<br>290                    295                    300 | 912 |
| acc ctg att att ccg aaa gat cgt cgc agc acc ggt aaa agc tgg ggt<br>Thr Leu Ile Ile Pro Lys Asp Arg Arg Ser Thr Gly Lys Ser Trp Gly<br>305                    310                    315                    320 | 960 |
| aaa ccg ggc ttc ctc atc gat agc ttg cat atc aac cag cga gcc gtc<br>Lys Pro Gly Phe Leu Ile Asp Ser Leu His Ile Asn Gln Arg Ala Val<br>                    325                    330                    335 | 1008 |
| gtt gca ccg gac aag gag gtc ctt tat gag gct ttt gat gag atg gag<br>Val Ala Pro Asp Lys Glu Val Leu Tyr Glu Ala Phe Asp Glu Met Glu<br>        340                    345                    350 | 1056 |
| ctc gcc atg ggc acc aac ccg aaa ccg gag cgt aaa agc aag cgt aac<br>Leu Ala Met Gly Thr Asn Pro Lys Pro Glu Arg Lys Ser Lys Arg Asn<br>                355                    360                    365 | 1104 |
| acc aac cgt aaa ccg cag gat att aaa ttc ccg ggt agt ggt cag gtg<br>Thr Asn Arg Lys Pro Gln Asp Ile Lys Phe Pro Gly Ser Gly Gln Val<br>370                    375                    380 | 1152 |
| gtg ggt ggt gtg tac ctg gtg ccg cgt cgt ggt ccg taaggatcc<br>Val Gly Gly Val Tyr Leu Val Pro Arg Arg Gly Pro<br>385                    390                    395 | 1197 |

-continued

<210> SEQ ID NO 11
<211> LENGTH: 396
<212> TYPE: PRT
<213> ORGANISM: Artificial Sequence
<220> FEATURE:
<223> OTHER INFORMATION: Amino acid sequence coding for chimeric antigen.

<400> SEQUENCE: 11

```
Glu Phe Thr Lys Val Pro Val Ala Tyr Ala Ala Lys Gly Tyr Lys Val
1               5                   10                  15

Leu Val Leu Asp Pro Ser Val Ala Ser Thr Leu Gly Phe Gly Ala Tyr
            20                  25                  30

Leu Ser Lys Ala His Gly Val Asn Pro Asn Ile Arg Thr Gly Ile Arg
        35                  40                  45

Thr Val Thr Thr Gly Ala Pro Val Thr Tyr Ser Thr Tyr Gly Lys Tyr
    50                  55                  60

Leu Ala Asp Gly Gly Cys Ala Gly Gly Ala Tyr Asp Val Ile Gly Ser
65                  70                  75                  80

Gly Glu Glu Val Ala Leu Ser Asn Thr Gly Glu Val Pro Phe Tyr Gly
                85                  90                  95

Arg Ala Ile Pro Ile Glu Ala Ile Lys Gly Gly Arg His Leu Val Phe
            100                 105                 110

Cys His Ser Lys Glu Lys Cys Asp Glu Leu Ala Ser Ala Leu Ser Gly
        115                 120                 125

Leu Gly Leu Asn Ala Val Ala Phe Tyr Arg Gly Leu Asp Val Ser Ile
    130                 135                 140

Ile Pro Thr Gln Gly Asp Val Val Ile Val Ser Thr Asp Ala Leu Met
145                 150                 155                 160

Thr Gly Phe Thr Gly Asp Phe Asp Ser Val Val Asp Cys Asn Thr Cys
                165                 170                 175

Ile Thr Gln Gly Ser Gly Leu Val Ser Phe Ala Ser His Val Pro Tyr
            180                 185                 190

Ile Glu Gln Gly Met Gln Leu Ser Glu Gln Phe Lys Gln Lys Ser Leu
        195                 200                 205

Gly Leu Leu Gln Thr Ala Thr Lys Gln Ala Glu Ala Ala Pro Val
    210                 215                 220

Val Gly Thr Pro Lys Ser Arg Arg Pro Glu Gly Arg Ala Trp Ala Gln
225                 230                 235                 240

Pro Gly Thr Ile Ile Leu Ser Gly Arg Pro Ala Val Val Pro Asp Arg
                245                 250                 255

Glu Val Leu Tyr Gln Glu Phe Leu Glu Ala Ser Arg Ala Ala Leu Ile
            260                 265                 270

Glu Glu Gly Gln Arg Ile Ala Glu Met Leu Lys Ser Lys Ile Gln Gly
        275                 280                 285

Leu Leu Gln Gln Ala Ser Lys Gln Ala Gln Asp Ile Lys Ile Asp Gly
    290                 295                 300

Thr Leu Ile Ile Pro Lys Asp Arg Arg Ser Thr Gly Lys Ser Trp Gly
305                 310                 315                 320

Lys Pro Gly Phe Leu Ile Asp Ser Leu His Ile Asn Gln Arg Ala Val
                325                 330                 335

Val Ala Pro Asp Lys Glu Val Leu Tyr Glu Ala Phe Asp Glu Met Glu
            340                 345                 350

Leu Ala Met Gly Thr Asn Pro Lys Pro Glu Arg Lys Ser Lys Arg Asn
        355                 360                 365
```

```
                                        -continued
Thr Asn Arg Lys Pro Gln Asp Ile Lys Phe Pro Gly Ser Gly Gln Val
    370                 375                 380

Val Gly Gly Val Tyr Leu Val Pro Arg Arg Gly Pro
385                 390                 395
```

METHOD FOR MEASUREMENT OF HEPATITIS C VIRUS

FIELD OF THE INVENTION

The present invention relates to a method for detection of the hepatitis C virus (HCV), and more specifically it relates to a method for measurement of HCV core antigen or for simultaneous measurement of HCV core antigen and HCV core antibodies. The method is particularly effective for screening of multiple blood samples and the like.

BACKGROUND ART

Hepatitis caused by infection with HCV (hepatitis C virus) becomes chronic with high incidence, and as the infection period is prolonged it often progresses to liver cirrhosis and hepatocellular carcinoma. However, since infection with HCV occurs mainly through blood and blood-derived components, it is possible to identify and eliminate the source of infection to block the infection route. Current methods of identifying infection sources are primarily methods of detecting antibodies against HCV polypeptides, but methods are being sought that can identify infection sources with greater accuracy.

Such methods are being sought because of the existence of a period of time known as the "window period" after HCV infection during which the antigen is present but antibodies are not yet produced. Antibody testing cannot determined whether serum taken during this period is infected or not. Therefore, there is a risk of secondary infection by the blood derived components, such as blood donation, blood components, factors from blood, contaminated specimens in the window period, because blood donor is screened by the antibody test that can not exclude such specimens. For this reason it has been necessary to detect HCV itself, that is, HCV particles, instead of antibodies against HCV polypeptides to reduce the risk.

Detection and measurement of HCV itself is possible by detecting antigens or genome (RNA) in the HCV particles. Here, an antigen in the HCV particles could be core antigen or an envelope antigen (E1, E2).

A lot of vanants were reported in the antigenic region of envelope protein such as hyper variable region. In addition, heterogeneities of sequences between genotypes were reported. In order to detect all of these variants and heterogeneous sequences, it is necessary to use probes that bind to several regions respectively.

Here, "probe" will be used to refer to a molecule that binds specifically to an antigen, for example a molecule which recognizes and binds to an antigen molecule, such as a receptor, antibody, recombinant antibody, functional molecule or functional structure.

The amino acid sequences of core antigen were more conserved than those of envelope antigens. By selecting well conserved regions among several HCV genotypes, a probe recognizing core antigen of all genotype could be obtained. Consequently, the method whose results should not be affected by genotypes will be constructed.

However, one point must be considered in constructing systems for detection of antigens. Specifically, it is highly possible that antibodies in specimens from the subject compete with the antigen-detecting probe for the binding sites, resulting in lowering the detection of sensitivity for the antigen by interfering probe binding. A method would be constructed by using probes recognizing the regions that could not be bound or interfered by antibodies in the specimens. However, it is difficult to prepare probes that fulfill these conditions for molecules reported to have multiple antibody-binding sites, such as HCV core antigen.

Thus, detection of antigen molecules requires elimination of antibodies that inhibit probe binding. Methods of elimination include methods of elimination based on physical principles, for example methods utilizing differences in molecular weight for separation and fractionation of HCV particles and antibodies. Examples of such methods include gel filtration, ultracentrifugation, density gradient centrifugation and molecular weight fractionation using membranes such as ultrafiltration membranes. However, since antibodies often form complexes with other biomolecules whereby they become high molecular weight entities, their separation from HCV particles is difficult by methods based on physical principles. These methods also employ special equipment during the processing steps, which makes their application difficult for mass screening, such as blood screening.

HCV particles are preferentially precipitated by the difference of their solubility in water-based solution containing PEG (polyethylene glycol), which alter the microenvironment of water. However, it will be very difficult to separate antibodies and their complex with antigens from HCV particles, because these components precipitated in same fractions. Moreover, HCV particles often form immune complexes between the antigens in the HCV particles and antibodies that recognize them, and it is difficult to separate only the antibodies or antigens from the immune complexes.

The methods implemented are therefore ones whereby substances (antibodies, etc.) that inhibit probe functions are eliminated by destroying their functions. One such method for losing antibody functions is a method in which the antibody protein is denatured by exposure to conditions that denature the protein structure, but it is essential here to destroy the function of the antibody while not eliminating the function of the object antigen, i.e. the function of binding with the probe, which means not losing the epitope or allowing the epitope to be displayed again, if the probe is an antibody.

The target function of a method of determining the HCV infection will differ depending on the goal.

Antibody testing is a method only to determine the specimen containing antibodies against HCV. When antibodies against HCV are present in a specimen, there are cases where the specimen donor is currently contains HCV because of active injection of HCV, while there are other cases where the specimen does not contain HCV because of HCV elimination from body by treatment or material recovery it is difficult to discriminate these therefore cases based on the presence or absence of antibodies.

The important function of antigen test is to determine whether or not HCV is present in a specimen or to indicate the level of HCV when it is present. It is not dependent on the question of whether or not antibodies are present.

For treatment, HCV antibody testing provides important information for determining whether HCV is the main cause of hepatitis. However, the test for HCV itself is require for definite diagnosis. Determining whether HCV has been eliminated from the body is important in judging the efficacy of treatment. The information of the level of antigen is essential in making a such decision for treatment. That is, for treatment it is important to know whether or not and at what level the antigen is present, regardless of the presence or absence of antibodies. For treatment, then, the most important testing methods are those which indicate the presence or absence and the level of antigen.

For blood and blood-derived components, preventing secondary infection is of greatest importance. For this purpose, testing methods that assess the risk of HCV infection. Antibody testing is currently being used as the primary testing method in this field.

However, as explained above, antibody testing cannot determine whether serum is infected during the window period after HCV infection. Consequently, when blood-derived substances such as transfusion and blood components, blood preparations, etc. are utilized for screening by antibody testing, there is a risk of secondary infection by specimens in the window period.

Coupling this with antigen testing is desired in order to reduce this risk, but antigen testing is still not implemented for mass screening for blood donation.

If a testing method existed that could determine the presence or absence of antigen with a theoretical accuracy (sensitivity, specificity) of 100%, that method could be used as the sole testing method. However any method have a limit of the detection sensitivity and cannot measure levels below that detection sensitivity. Thus, no testing method exists that can discriminate with 100% accuracy. There remains the possibility of missing the source of infection by antigen testing alone, and it is for this reason that measurement of both antibody and antigen is necessary to reduce the risk of secondary infection. If the antigen test, having high sensitivity and specificity sufficient for mass screening, is available, both antigen and antibody test were required for the screening. This requirement will result in higher cost of the screening, because the number of tests performed with samples should increase than present.

It is therefore clear that if measurement of antigen and antibody by the same method becomes possible, it will allow a reduction in the number of tests performed in the field, thus providing a major effect.

As already mentioned, despite the development of antibody detecting methods and antigen detecting methods, when it is attempted to detect antigen under conditions for detecting antibodies as alluded to above, the antigen cannot be efficiently detected because of the presence of antibodies which inhibit binding of probes that detect the antigen. Even under conditions for detection of antigen, however, the adopted methods eliminate antibodies that compete against detection of antigen, as explained above, and therefore antibodies cannot be detected. The currently reported methods, therefore, do not allow detection of antigen and antibody by a single method.

DISCLOSURE OF THE INVENTION

For the purpose of reducing secondary infection when utilizing blood and materials derived from blood, it is not necessary to distinguish between infected persons and formerly infected persons, as it is sufficient to be able to determine whether or not antibody or antigen is present. The present invention therefore provides a method of detecting antigen in specimens during periods in which they contain no antibodies, such as during window periods, and detecting the antigen or the antigen and antibodies in specimens during periods in which the antibodies are present; it therefore provides a new testing method which is desirable for testing of blood and blood-derived substances.

In order to solve the problems mentioned above, the present invention provides a method for measurement of the hepatitis C virus (HCV), characterized by measuring HCV core antigen by its binding with one or more probes in the presence of one or more detergents with one or more alkyl chains and one or more secondary to quaternary amines or one or more non-ionic detergents, or both.

The present invention further provides a method for measurement of HCV core antigen by the aforementioned method while also measuring HCV core antibody by its binding with a probe.

EMBODIMENTS FOR CARRYING OUT THE INVENTION

The method of detecting HCV infection provided by the present invention is a method whereby the antigen is detected in a specimen during a period in which no antibodies are present, such as during a window period, and whereby the antigen or both the antibody and antigen are detected during periods in which antibodies are present. In other words, during window periods in which no antibodies are present, the fact that no antibodies are present means that there is no need to eliminate antibodies during detection of the antigen. Consequently, pre-processing for detection of the antigen is no longer necessary.

Nevertheless, the regions on the antigen, that are recognized by the probe, must be displayed for detection, because the core antigens are packaged into virus particle. HCV particles are believed to have a structure wherein complexes are formed between the genomic RNA and the core antigen, forming particles which are coated with lipid outer membranes comprising envelope proteins. They are also believed to exist in the blood in the form of complexes with low density lipoproteins (LDLs) and or anti-HCV antibodies. The probe cannot recognize and bind with the core antigen when it is in the viral particles present in the blood. Thus, detection of core antigen requires processing to remove the structure enveloping the core antigen to allow recognition of the core antigen by the probe.

The present invention therefore further provides a reaction method comprising reaction conditions and a reaction system by which core antigen in HCV particles contained in a specimen is displayed so that it can be recognized by a probe for recognition of the core antigen, as well as a reagent that includes such a reaction system.

During periods in which antibodies are present at a sufficient level, antibodies against the core antigen that compete for the binding site of the probe are sometimes present in the specimen, and this can lower the detection sensitivity for the core antigen. Also, when the core antigen is exposed to allow the probe to bind in the presence of the antibodies to compete with the probe for the binding, the levels of antibodies that bind the antigen for the antibody test will be reduced by their absorption to the displayed core antigen of the virus particles. As a result, the sensitivity of the antibody test, which measure the amount of immunocomplex of antibodies with the antigens for the antibody test.

Consequently, while the antigen used for detection of HCV antibodies may be one consisting solely of the core antigen epitope, it is preferably a peptide or polypeptide including an HCV epitope other than the core antigen. It may also be a peptide or polypeptide, or compound, other than the peptide or polypeptide including the HCV epitope, which mimics the HCV epitope.

However, the probe used for detection of the core antigen and the HCV epitope or the compound substituting for the HCV epitope are preferably not entities that bind through mutual recognition.

The antibody used as the probe for the HCV core antigen or the labeled antibody for detection of the HCV core antigen may be a polyclonal antibody obtained by immunization of an experimental animal such as a mouse, rabbit, chicken, goat, sheep, cow, etc.; a monoclonal antibody produced by a hybridoma obtained by separating spleen cells from an immunized individual and fusing them with myeloma cells; a monoclonal antibody produced by spleen cells or blood leukocytes that have been immortalized with the EB virus; or a monoclonal antibody produced by a human or chimpanzee infected with HCV; a recombinant antibody produced by cells transformed by a recombinant antibody gene constructed by combining an immunoglobulin constant region gene fragment with a variable region gene fragment obtained from immunoglobulin cDNA or chromosomal DNA from a mouse, human, etc., a variable region gene fragment constructed by combining a portion of immunoglobulin cDNA or chromosomal DNA with an artificially created sequence, a variable region gene fragment constructed using an artificial gene sequence or a variable region gene fragment created by a gene recombination method using these as materials; a phage antibody created by fusing any of the aforementioned variable region gene fragments with the structural protein of a bacteriophage, for example; or a recombinant antibody produced by cells transformed by a recombinant antibody gene constructed by combining any of the aforementioned variable region gene fragments with another appropriate gene fragment, such as a portion of the myc gene.

Probes produced by artificial introduction of variable regions into trypsin molecules, probes obtained by artificially modifying molecules that bind specifically to proteins such as receptors, and other probes prepared by combinatorial chemistry techniques, may be used so long as they exhibit high specificity and affinity for the core antigen.

The above-mentioned monoclonal antibodies can be easily prepared by those skilled in the art. Preparation of monoclonal antibodies from hybridomas is well-known. An example thereof is periodic immunization of BALB/c mice or the like either intraperitoneally or intradermally using the fused polypeptide or polypeptide (hereunder referred to as "the present antigen") as an antigen either alone or bound to BSA, KLH or the like, in simple form or in admixture with an adjuvant such as Freund's complete adjuvant. The present antigen is administered through the caudal vein as a booster immunization once the blood antibody titer has increased, and after antiseptic extraction of the spleen, cell fusion is carried out with an appropriate mouse myeloma cell line to obtain hybridomas. This method can be carried out according to the method of Kohler and Milstein (Nature 256: 495-497, 1975).

The hybridoma cell lines obtained by the above procedure are cultured in a suitable culture solution, and then a hybridoma cell line producing antibodies that exhibit specific reaction with the present antigen is selected and cloned. The cloning of the antibody-producing hybridoma may be accomplished by the limiting dilution method, or the soft agar method (Eur. J. Immunol. 6: 511-519, 1976). The monoclonal antibody produced is purified by a method such as column chromatography using Protein A, etc.

A molecule to be used as a probe may be prepared instead of the aforementioned monoclonal antibody. For example, recombinant antibodies are discussed in detail in a general outline by Hoogenboon (Trends in Biotechnology, 15: 62-70, 1997).

According to the invention, the antigen used as a probe for HCV core antibodies in a specimen or the antigen used for production of the HCV core antibodies is, specifically, a polypeptide having an amino acid sequence represented for example by SEQ. ID. No. 1 or No. 2, or a fused polypeptide including one of the amino acid sequences listed as SEQ. ID. Nos. 3 to 6, and these can be obtained by recombinant expression of DNA coding therefor.

The principle for detection in this case may be a method commonly used for immunoassay, such as the enzyme-labeled antibody method, fluorescent labeling method, radioisotope labeling method, etc., and the principle for enzyme detection in the enzyme-labeled antibody method is the colorimetric method, fluorescent method, chemiluminescence method, etc. The method used for detection of the antibody may be one which is commonly employed for antibody detection, such as the double-antigen sandwich method, and a one-step sandwich system may likewise be used for detection of the antigen as well.

One mode of the invention is the reaction system described below. (1) A probe for the HCV core antigen, for example antibodies for the HCV core antigen, and (2) a compound comprising the HCV epitopes, for example a peptides, peptide compounds or polypeptides comprising the HCV epitopes, or a mixture thereof, are immobilized on a carrier used for immunoassay, such as a microtiter plate. In order to capture core antigens and HCV antibodies in the specimen, the immobilized carrier is reacted with the specimens in the solution that contains the compounds to expose the core antigen in the virus particles or complexes with the particles and not to inhibit the function of HCV antibodies for binding to the HCV epitopes.

After then removing the unbound components in the specimen by, for example, washing the carrier with a suitable buffer solution, it is reacted with a reaction solution containing probes that recognizes the core antigen bound to the carrier, for example an enzyme-labeled antibodies for the core antigen, and probes that recognizes an antibody for the HCV epitope bound to the carrier, for example an enzyme-labeled anti-human antibody mouse monoclonal antibody, to cause specific binding with the core antigen and the antibodies to the HCV epitopes captured the carrier. After the reaction, the carrier is washed with a suitable buffer solution to remove the unreacted components, and detection of the label by an appropriate method will allow detection of the core antigen and the antibodies to the HCV epitope, which are present in the specimen.

It will be readily apparent to researchers in the relevant field that this may be applied as well to B/F separation methods that can be used for common immunoassay methods, such as immunochromatography.

Reaction Conditions Suitable for Antigen Detection

The reaction system suitable for antigen detection in the system provided by the present invention is a system under mild conditions which will not destroy the function of the antibody to the HCV epitopes, while also being under conditions that will sufficiently expose the region recognized by the antibody probe which is to recognize the HCV antigen amidst the HCV particles that are exist as a complex structure in the specimen.

It has been demonstrated that core antigen can be detected if the viral particles that have been separated by ultracentrifugation (Takahashi et al., 1996, J. Gen. Virol., 73:667-672) or HCV particles which have been aggregated and precipitated with polyethylene glycol are treated with a non-ionic detergent such as Tween80 or Triton X100 (Kashiwakuma et al., 1996, J. Immunological Methods 190:79-89); in the former case, however, the detection sensitivity is insufficient and it is doubtful whether sufficient antigen is exposed. In the latter case, treatment agents other than detergents were added to inactivate the antibodies. In addition nothing is mentioned about the actual effect of the detergent.

For the present invention, the conditions were first studied on the basis of the detergent, and by preparing reaction solutions with detergent-based compositions, and it has become possible to efficiently detect antigen in HCV particles by simply diluting the specimen with the reaction solution without applying pre-processing involving procedures such as centrifugation and heating as in hitherto reported HCV antigen detection systems.

In order to construct the system which this invention provide, it is necessary to effectively extract the core antigen from the viral particles, suppress interaction between the various substances in the serum, and provide conditions which allow efficient reaction between the probe and the antigen. As detergents which are effective for this purpose there may be mentioned detergents with alkyl groups and secondary to quaternary amines in the same molecule, and non-ionic detergents.

In a detergents comprising with alkyl chains and secondary to quaternary amines, the alkyl chain is preferably a linear alkyl chain, with the number of carbon atoms being preferably 10 or greater and more preferably 12-16. The amine is preferably a tertiary amine or quaternary amine (ammonium). As specific detergents there may be mentioned dodecyl-N-sarcosinic acid, dodecyltrimethylammonium salts, cetyltrimethylammonium salts, 3-(dodecyldimethylammonio)-1-propanesulfonic acid, 3-(tetradecyldimethylammonio)-1-propanesulfonic acid, dodecylpyrimidium salts, cetylpyrimidium salts, decanoyl-N-methylglucamide (MEGA-10), dodecyl-N-betaine, and the like. Dodecyl-N-sarcosinic acid and dodecyltrimethylammonium salts are preferred.

The aforementioned non-ionic detergent is preferably one with a hydrophilic-lipophilic balance of 12 to 14, with polyoxyethylene isooctyl phenyl ethers such as Triton X100, Triton X114, etc. and polyoxyethylene nonyl phenyl ethers such as Nonidet P40, Triton N101, Nikkol NP, etc. being preferred.

According to the invention the above-mentioned two types of detergents may be used alone, but their combinations are more preferable since synergistic effects can be achieved.

The present inventors found that a carrier, which was immobilized antigens containing HCV epitopes for detection of HCV antibodies and antibodies to HCV antigens for the detection of HCV antigen, is able to efficiently capture HCV antigen, HCV antibodies in the specimens without HCV antibodies, or HCV antigen, respectively. The inventors also found that the carrier efficiently capture both HCV antigens and antibodies in the specimens containing HCV antigens and antibodies, and gave higher signals derived by their binding. Based upon these findings, the inventors have completed the present invention.

A method for simultaneously detecting an viral antigen and antibodies to virus related portion has been already reported for HIV (Weber et al., J. Clinic. Microbiol., 36: 2235-2239, 1998). In the case of HIV, it is effective to detect p24 which is gag protein for a viral antigen test. On the other hand, for test for an antibody against viral antigen, it is effective to detect antibodies against envelop protein and p19 which is a gag protein. Therefore, a method for simultaneously detecting a viral antigen and an antibody against viral antigen is established by combining an antigen test which detects g24 that is a gag protein, and an antibody test which detects antibodies against envelop protein and p19 that is a part of gag protein.

In such a case wherein epitopes used for detection of viral antigens is different from epitopes recognized by antibodies in a specimen used for detection of viral antibodies, it is relatively easy to construct a method for simultaneously detecting viral antigens and an antibodies against viral antigens. This is because, for example, in the case of HIV test, the antigen p24 recognized by a probe for detection of the antigen, for example, a monoclonal antibody against HIV epitope, and antigens recognized by antibodies contained in a specimen from a patient, which are envelop protein and p19 that is a part of the gag protein are different proteins, and therefore the probe used for the antigen test cannot recognize the envelop protein and the p19 which is a part of the gag protein. Accordingly, there is no interference between the antigen detection system and the antibody detection system, for example a non-specific reaction, decrease in sensitivity caused by competitive reaction between the probe and HIV epitope used for antibody detection.

However, for detection of antibodies against HCV epitopes, the detection of antibodies against core antigen is highly useful from a clinical point of view (Chiba et al., Proc. Natl. Acad. Sci. USA 88: 4641-4645, 1991; Bresters et al., Vox Sang, 62: 213-217, 1992). Therefore, it is essential for the antibody detection to detect an antibodies against the core antigen epitopes. On the other hand, for the antigen detection, detection of the core antigen is most useful in detection of HCV antigens, because, of antigens which form viral particles, the mutation rate of the core antigen is lower than that of other antigens such as E1 and E2. Namely, to construct an assay system which simultaneously detects HCV antigen and HCV antibodies, the same antigen, i.e., the core antigen must be used for both the antigen detection system and the antibody detection system.

Therefore, if the core antigen is used without any improvement, the following problems are caused: a monoclonal antibody against the core antigen used for the detection of antigen binds to the core antigen used for the detection of antibody, resulting in decrease in sensitivity for detection of core antigen in a specimen; the monoclonal antibody binds to the antigen used for the detections of antibody resulting in nonspecific reaction in the antigen test; and the HCV epitope for the antibody test is masked resulting in decrease in sensitivity.

To solve the above-mentioned problems, the present inventors found that both the antigen and antibodies can be efficiently detected simultaneously by distinguishing the epitopes recognized by monoclonal antibody in the antigen detection from the epitopes of the core antigen for antibodies present in the specimen, and completed the present invention.

An combination of epitopes suitable for simultaneous detection of the antigen and antibodies is shown in detail in Examples described hereinafter.

Regarding the epitopes for antibodies in a specimen against the core antigen, various epitope analysises show that the most important regions are present at the N-terminal region of the core antigen, especially from the position 1 to the position 40 of the HCV polypeptide (Okamoto et al., Hepatology 15: 180-186, 1992; Sallsberg et al. J. Clinical. Microbiol., 30: 1989-1994, 1992; Sallsberg et al., J. Med. Vilol. 43: 62-68, 1994). In addition, an epitope which genotype-specifically reacts is present in the region from the position 60 to the position 80 of the HCV polypeptide (Machida, Hepatology, 16: 886-891, 1992; Japanese Patent Application 9-209522). Therefore, it is important that an antigen for detection of antibodies against the HCV epitopes has a sequence from the position 1 to the position 40 and from the position 66 to the position 80 of the HCV polypeptide. Accordingly, Example discloses an antigen polypeptide "CEPM" having the sequence from the position 1 to the position 42 and from the position 66 to the position 80 of the HCV polypeptide as an antigen for detection of HCV antibodies. Note that the CEPM is an antigen having an artificial sequence comprising the following regions of the HCV polypeptide in the described order, and a process for construction thereof is described in Japanese Patent Application No. 9-209522. The sequence thereof is described in SEQ ID NO:10.

The linkage of the HCV epitopes of CEPM:
(1238-1312)-(1363-1460)-(1712-1751)-(66-80)-(1686-1704)-(1716-1751)-(66-80)-(1690-1713)-(1-42)

On the other hand, for the detection of antigen, monoclonal antibodies recognizing and binding to the region from the position 100 to the position 130 of the HCV polypeptide, antibodies against which region are relatively rare in specimens, is used as a primary antibody, and to detect the core antigen captured by the primary antibody, a monoclonal antibody recognizing a region from the position 40 to the position 50 of the HCV polypeptide, which region is not used for the detection of antibody, is used as a secondary antibody.

Both the above-mentioned monoclonal antibodies do not bind to the antigenic region from the position 1 to the position 42 of the HCV polypeptide, which is used for the detection of HCV antibodies, and therefore by using the above-mentioned antibodies and antigen, no reaction interference occurs in the antigen detection system and the antibody detection system, and both the detection systems can simultaneously function.

EXAMPLES

The invention will now be explained in detail by way of the following examples.

Example 1

Expression of HCV-Derived Polypeptide and Purification (A) Construction of Expression Plasmid An expression plasmid corresponding to the HCV core region was constructed in the following manner. One microgram each of DNA of plasmids pUC•C11-C21 and pUC•C10-E12 obtained by incorporating clone C11-C21 and clone C10-E12 (Japanese Unexamined Patent Publication No. 6-38765) into plasmid pUC119 were digested at 37° C. for one hour with 20 µl of a restriction enzyme reaction solution [50 mM Tris-HCl (pH 7.5), 10 mM MgCl$_2$, 1 mM DTT, 100 mM NaCl, 15 units of EcoRI and 15 units of ClaI enzyme] and [10 mM Tris-HCl (pH 7.5), 10 mM MgCl$_2$, 1 mM DTT, 50 mM NaCl, 15 units of ClaI and 15 units of KpnI], respectively, and this was followed by electrophoresis on 0.8% agarose gel to purify an approximately 380 bp EcoRI-ClaI fragment and an approximately 920 bp ClaI-KpnI fragment.

To these DNA fragments and a vector obtained by digesting pUC119 with EcoRI and KpnI there were added 5 µl of a 10× ligase buffer solution [660 mM Tris-HCl (pH 7.5), 66 mM MgCl$_2$, 100 mM dithiothreitol, 1 mM ATP], 1 µl of T4 ligase (350 units/µl) and water to 50 µl, and this was followed by overnight incubation at 16° C. for ligation reaction. The plasmid was used to transform E. coli JM109, obtaining plasmid pUC•C21-E12.

A 1 ng portion of DNA of this plasmid pUC•C21-E12 was subjected to PCR using two primers (5'-GAAT-TCATGGGCACGAATCCTAAA-3' (SEQ. ID. No. 7), and 5'-TTAGTCCTCCAGAACCCGGAC-3' (SEQ. ID. No. 8)). The PCR was conducted using a GeneAmp™ Kit (DNA Amplification Reagent Kit, product of Perkin Elmer Cetus) under conditions of DNA denaturation at 95° C. for 1.5 minutes, annealing at 50° C. for 2 minutes and DNA synthesis at 70° C. for 3 minutes, and the resulting DNA fragment was separated by 0.8% agarose gel electrophoresis and purified by the glass powder method (Gene Clean).

Separately, pUC19 was digested with restriction enzyme SmaI, and the DNA fragment obtained by PCR was added to 5 µl of a 10× ligase buffer solution [660 mM Tris-HCl (pH 7.5), 66 mM MgCl$_2$, 100 mM dithiothreitol, 1 mM ATP] and 1 µl of T4 ligase (350 units/µl) with water to 50 µl, after which overnight incubation was performed at 16° C. for ligation reaction. The plasmid was used to transform E. coli JM109, obtaining plasmid pUC19•C21-E12•SmaI.

One microgram of this plasmid DNA was digested at 37° C. for one hour with 20 µl of a restriction enzyme reaction solution [150 mM NaCl, 6 mM Tris-HCl (pH 7.5), 6 mM MgCl$_2$, 15 units of EcoRI and 15 units of BamHI enzyme], and this was followed by 0.8% agarose gel electrophoresis to separate an approximately 490 bp EcoRI-BamHI fragment, which was then purified by the glass powder method.

A 1 µg portion of DNA of the expression vector Trp•TrpE (Japanese Unexamined Patent Publication No. 5-84085) was then digested at 37° C. for one hour with 20 µl of a restriction enzyme reaction solution [150 mM NaCl, 6 mM Tris-HCl (pH 7.5), 6 mM MgCl$_2$, 15 units of EcoRI and 15 units of BamHI enzyme], and after adding 39 µl of water to the reaction solution and heating it at 70° C. for 5 minutes, 1 µl of bacterial alkali phosphatase (BAP) (250 units/µl) was added prior to incubation at 37° C. for one hour.

Phenol was added to the reaction solution for phenol extraction, and DNA in the resulting aqueous layer was precipitated with ethanol and dried. A 1 µg portion of the obtained EcoRI-BamHI treated vector DNA and the aforementioned core fragment were added to 5 µl of a 10× ligase buffer solution [660 mM Tris-HCl (pH 7.5), 66 mM MgCl$_2$, 100 mM dithiothreitol, 1 mM ATP] and 1 µl of T4 ligase (350 units/µl) with water to 50 µl, and this was followed by overnight incubation at 16° C. for ligation reaction.

A 10 µl portion of this reaction solution was used to transform E. coli HB101. A competent E. coli strain for the transformation can be prepared by the calcium chloride method [Mandel, M. and Higa, A., J. Mol. Biol., 53, 159-162 (1970)]. The transformed E. coli was spreaded onto an LB plate (1% tryptone, 0.5% NaCl, 1.5% agar) containing 25

μg/ml of ampicillin, and was incubated overnight at 37° C. One loopful of colonies formed on the plate was taken and transferred to LB medium containing 25 μg/ml of ampicillin for culturing overnight at 37° C.

After centrifuging 1.5 ml of the cell culture solution and collecting the cells, mini-preparation of the plasmid DNA was carried out by the alkali method [Manniatis et al., Molecular Cloning: A Laboratory Manual, 1982)]. A 1 μg portion of the obtained plasmid DNA was digested at 37° C. for one hour with 20 μl of a restriction enzyme reaction solution [150 mM NaCl, 6 mM Tris-HCl (pH 7.5), 6 mM MgCl$_2$, 15 units of EcoRI and 15 units of BamHI enzyme] and subjected to agarose gel electrophoresis, and a Trp•TrpE core 160 expression plasmid producing an approximately 490 bp EcoRI-BamHI fragment was selected.

(B) Expression and Purification of Polypeptide Encoded by Clone Core 160

*E. coli* HB101 bearing expression plasmid Trp•TrpE core 160 was inoculated in 3 ml of 2YT medium (1.6% tryptone, 1% yeast extract, 0.5% NaCl) containing 50 μg/ml of ampicillin, and cultured at 37° C. for 9 hours. One milliliter of the culture solution was subcultured at 37° C. in 100 ml of M9-CA medium (0.6% Na$_2$HPO$_4$, 0.5% KH$_2$PO$_4$, 0.5% NaCl, 0.1% NH$_4$Cl, 0.1 mM CaCl$_2$, 2 mM MgSO$_4$, 0.5% casamino acid, 0.2% glucose) containing 50 μg/ml of ampicillin. Indoleacrylic acid was added to a final concentration of 40 mg/l at the point when OD600=0.3, and culturing was continued for 16 hours. The culture solution was subjected to centrifugation separation to collect the cells.

The cells were suspended by addition of 20 ml of buffer solution A [50 mM Tris-HCl (pH 8.0), 1 mM EDTA, 30 mM NaCl], and further centrifugation yielded 2.6 g of cells. These obtained cells were suspended in 10 ml of buffer solution A, and after disrupting the *E. coli* membranes by ultrasonic disruption they were centrifuged to obtain an insoluble fraction containing a fused polypeptide of the polypeptide encoded by HCV cDNA and TrpE. To this fraction there was added 10 ml of buffer solution A containing 6 M urea for solubilization and extraction of the fused polypeptide. The solubilized extract was subjected to ion-exchange column chromatography using S-Sepharose for purification of the fused polypeptide.

Example 2

Hybridoma Construction Method

The fused polypeptide (TrpC11) prepared by the method described above was dissolved in 6 M urea and then diluted in a 10 mM phosphate buffer solution (pH 7.3) containing 0.15 M NaCl to a final concentration of 1.0 mg/ml and mixed with an equal amount of TiterMax to make a TrpC11 suspension. The suspension was adjusted to a TrpC11 concentration of 0.01 to 0.05 mg/ml and used for intraperitoneal injection into 4- to 6-week-old BALB/c mice. After approximately 8 weeks the immunized animals were further injected through the caudal vein with a physiological saline solution prepared to a TrpC11 concentration of 0.005 to 0.03 mg/ml.

On the third day after the final booster immunization, the spleens of the immunized animals were aseptically extracted, sliced with scissors, broken into individual spleen cells using a mesh, and washed 3 times with RPMI-1640 medium. A logarithmic growth stage mouse myeloma cell line PAI which had been cultured for a few days in the presence of 8-azaguanidine and had the revertants completely removed washed in the same manner described above, after which $1.8 \times 10^7$ of these cells and $1.0 \times 10^8$ of the spleen cells were placed in a 50-ml volume centrifuging tube and mixed. This was subjected to centrifugal separation at 200×g for 5 minutes, the supernatant was removed off, and 1 ml of RPMI-1640 medium containing 50% polyethylene glycol (PEG) 4000 (product of Merck Co.) heated at 37° C. was added for cell fusion.

After removing the PEG from the fused cells by centrifugation (200×g, 5 minutes), a 96-well plate was used for culturing for 1 to 2 weeks in RPMI-1640 medium containing hypoxanthine, aminopterin and thymidine (hereunder abbreviated to "HAT"), to allow growth of only the hybridomas. They were then grown in HAT-free medium, and after about 2 weeks the ELISA method was used to search for clones producing the target antibody, upon which hybridomas were obtained which produced the monoclonal antibody of the invention having the desired reaction specificity.

A conventional limiting dilution procedure was followed to search for and monoclone the target antibody-producing strains among the obtained hybridomas, and the hybridomas were designated as HC11-14, HC11-10, HC11-3 and HC11-7. These four different hybridomas were deposited at the National Institute of Bioscience and Human Technology on Jul. 4, 1997 as FERM BP-6006, FERM BP-6004, FERM BP-6002 and FERM BP-6003.

Example 3

Preparation of Monoclonal Antibody

The hybridomas obtained by the method described in Example 2 were transplanted into mice abdomens treated with pristane, etc., and the monoclonal antibodies that were gradually produced in the ascites were collected. The monoclonal antibodies were purified by separating the IgG fraction with a Protein A bound Sepharose column.

The isotype of the monoclonal antibodies produced by the above-mentioned four different hybridomas, C11-14, C11-10, C11-7 and C11-3, were identified by the double immunodiffusion method using each isotype antibody of rabbit anti-mouse IG (product of Zymed Co.), and it was found that C11-10 and C11-7 were IgG2a, and C11-14 and C11-3 were IgG1. As a result of epitope analysis of these four monoclonal antibodies using 20 peptides synthesized by HCV/core region-derived sequences, they were shown to be monoclonal antibodies which specifically recognize portions of the core sequence as shown in Table 1.

TABLE 1

| Antibody | Recognition site |
| --- | --- |
| C11-14 | $^{41}$Gly-$^{50}$Arg (SEQ. ID. No. 4) |
| C11-10 | $^{21}$Asp-$^{40}$Arg (SEQ. ID. No. 3) |
| C11-3 | $^{100}$Pro-$^{120}$Gly (SEQ. ID. No. 5) |
| C11-7 | $^{111}$Asp-$^{130}$Phe (SEQ. ID. No. 6) |

Example 4

Method for Efficient Detection of Antigen without Pre-Processing Procedure

A specimen containing HCV particles was diluted in a containing detergents reaction solution to determine the efficiency with which HCV core antigen was detected.

The detection of the HCV core antigen was performed by the sandwich enzyme immunoassay (EIA) using monoclonal antibodies for the HCV core antigen. Of the monoclonal antibodies obtained in Example 3, C11-3 and C11-7 were used as antibodies for captureing the core antigen, and C11-10 and C11-14 were used as antibodies for detection of the captured core antigen.

The EIA was performed basically under the following conditions. Solutions of monoclonal antibodies C11-3 and C11-7 in acetate buffer solutions diluted to 4 μg/ml each were added to microtiter plates and incubated overnight at 4° C. They were then washed with a phosphate buffer solution and subjected to a blocking procedure by addition of phosphate buffer solution containing 1% BSA. After adding 100 μl of the reaction solution and 100 μl of the specimen thereto and mixing, the reaction was carried out at room temperature for 1.5 hours. After removing the unreacted materials by washing with a phosphate buffer solution containing a low concentration of detergent, monoclonal antibodies C11-10 and C11-14 labeled with alkali phosphatase were added for reaction at room temperature for 30 minutes. After completion of the reaction, the unreacted materials was removed by washing with a phosphate buffer solution containing a low concentration of detergents, and a substrate solution (CDP-Star/emerald11) was added for reaction at room temperature for 15 minutes, after which the luminescence was measured.

Different detergents were added to the primary reaction solution and their effects were examined. HCV antigen-positive serum with an anti-HCV antibody titer below the detection level and thought to contain virtually no anti-HCV antibody was used, and the core antigen detection sensitivities were determined based on the degree of luminescence and expressed as reaction ratios relative to 1.0 as the luminescence for healthy human serum. The results are shown in the following Tables 2 and 3.

TABLE 2

| | | HLB value | % | Reaction ratio (S/N ratio) for each serum with respect to healthy human serum | | | | |
|---|---|---|---|---|---|---|---|---|
| | | | | No. 45 | No. 46 | No. 3 | No. 7 | No. 19 |
| Not added | | | | 15.67 | 1.00 | 1.15 | 1.34 | 1.19 |
| Effect judgment criterion | | | | >30.0 | >2.0 | >2.0 | >2.0 | >2.0 |
| Additive | | | | | | | | |
| Anionic detergent | sodium dodecyl sulfate | 40.0 | 0.5 | 5.42 | | | | |
| | | | 2.0 | 5.73 | | | | |
| | sodium dodecyl-N-sarcosinate | | 0.5 | 12.79 | 2.70 | | | |
| | | | 2.0 | 125.43 | 7.27 | 3.83 | 3.70 | 6.71 |
| | perfluoroalkylcarboxylic acid S-113 (ASAHI GLASS) | | 0.5 | 10.55 | 1.27 | | | |
| | | | 2.0 | 6.72 | 0.91 | | | |
| Cationic detergent | cetyltrimethylammonium bromide | | 0.5 | 72.97 | 7.42 | 3.09 | 3.52 | 5.43 |
| | | | 2.0 | 44.55 | 5.35 | | | |
| | dodecylpyridinium chloride | | 0.5 | 53.43 | 4.70 | 2.05 | 1.52 | 2.33 |
| | | | 2.0 | 12.44 | 2.49 | | | |
| | n-dodecyltrimethylammonium | | 0.5 | 66.84 | 4.43 | 2.41 | 1.63 | 2.67 |
| | | | 2.0 | 27.98 | 3.77 | | | |
| | tetradecylammonium bromide | | 0.05 | 14.69 | | | | |
| | n-octyltrimethylammonium chloride | | 0.5 | 12.57 | | 1.00 | 0.75 | 0.99 |
| | | | 2.0 | 11.46 | | | | |
| Non-ionic detergent | CHAPS | | 0.5 | 29.57 | | | | |
| | | | 2.0 | 25.32 | | 1.63 | 1.82 | 2.42 |
| | perfluoroalkylbetaine 5-132 (ASAHI GLASS) | | 0.5 | 11.07 | 1.61 | | | |
| | | | 2.0 | 10.77 | 1.49 | | | |
| | 3-(dodecyldimethylammonio)-1-propanesulfonic acid | | 0.5 | 57.69 | | | | |
| | | | 2.0 | 113.19 | | 4.57 | 3.44 | 5.26 |

TABLE 3

| | | HLB value | % | Reaction ratio (S/N ratio) for each serum with respect to healthy human serum | | | | |
|---|---|---|---|---|---|---|---|---|
| | | | | No. 45 | No. 46 | No. 3 | No. 7 | No. 19 |
| Not added | | | | 15.67 | 1.00 | 1.15 | 1.34 | 1.19 |
| Effect judgment criterion | | | | >30.0 | >2.0 | >2.0 | >2.0 | >2.0 |
| Additive | | | | | | | | |
| Non-ionic detergent | MEGA-10 | | 0.5 | 32.11 | 3.38 | | | |
| | | | 2.0 | 38.49 | 3.53 | 1.97 | 1.87 | 2.84 |
| | Tween 20 | 16.7 | 0.5 | 16.88 | | | | |
| | | | 2.0 | 12.36 | | | | |
| | Tween 40 | 15.6 | 0.5 | 14.96 | | 1.02 | 0.99 | 1.41 |
| | | | 2.0 | 19.10 | | 1.32 | 1.25 | 1.64 |
| | Tween 80 | 15.0 | 0.5 | 12.45 | | 1.33 | 1.23 | 1.10 |
| | | | 2.0 | 17.47 | | | | |
| | Nonidet P-40 | 13.1 | 0.5 | 43.14 | | 3.09 | 2.95 | 4.58 |
| | octyl glycoside | | 0.5 | 12.48 | | 0.90 | 0.60 | 0.97 |
| | | | 2.0 | 25.07 | | 1.92 | 1.20 | 2.63 |
| | Triton N101 | 13.4 | 0.5 | 26.50 | | 1.85 | 1.62 | 2.70 |
| | | | 2.0 | 60.84 | | 2.23 | 2.28 | 3.81 |

TABLE 3-continued

| | | HLB value | % | Reaction ratio (S/N ratio) for each serum with respect to healthy human serum | | | | |
|---|---|---|---|---|---|---|---|---|
| | | | | No. 45 | No. 46 | No. 3 | No. 7 | No. 19 |
| | Triton X100 | 13.5 | 0.5 | 27.72 | | | | |
| | | | 2.0 | 71.08 | | 2.90 | 2.34 | 3.86 |
| | Triton X114 | 12.4 | 0.5 | 31.49 | | 2.04 | 1.65 | 2.77 |
| | | | 2.0 | 58.62 | | 1.92 | 2.11 | 2.51 |
| | Triton X305 | 17.3 | 0.5 | 10.50 | | 0.94 | 0.97 | 1.08 |
| | | | 2.0 | 25.91 | | 1.30 | 1.24 | 1.87 |
| | Triton X405 | 17.9 | 0.5 | 12.54 | | 0.86 | 0.78 | 1.04 |
| | | | 2.0 | 24.92 | | 1.21 | 1.24 | 1.25 |
| Others | benzyldimethylphenylammonium chloride | | 0.5 | 5.45 | 1.00 | | | |
| | | | 2.0 | 7.01 | 1.12 | | | |
| | triethylamine | | 0.5 | 3.89 | 0.97 | | | |
| Detergent mixture | 2% sodium dodecyl-N-sarcosinate + 2% Triton X100 | | | 244.13 | | 6.11 | 5.50 | 12.71 |

These results demonstrated that addition of non-ionic detergents exhibiting HLB values of 12 to 14, as represented by Triton X100, increased the luminescence and raised the detection sensitivity in HCV antigen-positive serum with respect to healthy human serum. It was also demonstrated that addition of detergents with both linear alkyl chains and secondary to quaternary amines in their structures, as represented by sodium dodecyl-N-sarcosinate and dodecyltrimethylammonium, also raised the detection sensitivity in HCV antigen-positive serum. No such sensitivity-raising effect was found with the surfactants having alkyl groups of 8 or fewer carbon atoms. Addition of a mixture of these two types of surfactants (mixture of 2% sodium dodecyl-N-sarcosinate+2% Triton X100 in Table 2) was also shown to raise the detection sensitivity in HCV antigen-positive serum.

Example 5

Core Antigen Detection in Specimens after HCV Infection and Before HCV Antibody Appearance (During Window Period)

A commercially available PHV905 seroconversion panel (BBI Inc.) was measured according to Example 4 with addition of 2% Triton X100 and 2% sodium dodecyl-N-sarcosinate to the reaction solution. The PHV905 panel used here exhibited positive conversion in the anti-HCV antibody test (Ortho EIA. 3.0) on the 21st day after initial observation (Serum No. PHV905-7), the antibody titer being represented by the cutoff index (S/CO), with 1.0 or greater judged as positive. The HCV core antigen activity (luminescence) was represented as a ratio (S/N) with respect to 1.0 as the luminescence for healthy human serum.

As shown in Table 4, core antigen activity was found even before anti-HCV antibody positivity, thus confirming that addition of the surfactant resulted in exposure of the core antigen from the viral particles, thus allowing its reaction with the immobilized monoclonal antibodies and its detection.

TABLE 4

| Serum No. | Days after initial observation | HCV core antigen activity (S/N) | Anti-HCV antibody titer (S/CO) |
|---|---|---|---|
| PHV 905-1 | 0 | 5.32 | 0.000 |
| 905-2 | 4 | 8.30 | 0.000 |
| 905-3 | 7 | 15.63 | 0.000 |
| 905-4 | 11 | 4.37 | 0.300 |
| 905-5 | 14 | 14.75 | 0.700 |
| 905-6 | 18 | 7.57 | 0.700 |
| 905-7 | 21 | 4.82 | 2.500 |
| 905-8 | 25 | 3.31 | 5.000 |
| 905-9 | 28 | 1.61 | 5.000 |

Example 6

Simultaneous Detection of HCV Antibody and Core Antigen in Specimen

A specimen (human serum) was used which contained an antibody for an HCV epitope but virtually no HCV antigen, and the following method was used to confirm that it was possible for the antibody for the HCV epitope to bind with the HCV polypeptide in the primary reaction solution containing the detergent without inactivation and for it to be detected by addition of anti-human antibody in a secondary reaction solution, and to confirm that it was possible to detect the core antigen when the core antigen was present, the antibody when the antibody for the HCV epitope was present, and both when both were present.

The EIA was performed basically under the following conditions. Recombinant antigen CEPM containing an HCV epitope was diluted in a urea-containing phosphate buffer solution, and then added to a microtiter plate and incubated overnight at 4° C. After washing with a phosphate buffer solution, a solution prepared by diluting monoclonal antibodies C11-3 and C11-7 in an acetate buffer solution was added to the plate and incubated overnight at 4° C. The method of preparing the recombinant antigen CEPM is described in Japanese Patent Application No. 9-209522. After removal of the antibody solution, it washed with a phosphate buffer solution and subjected to a blocking procedure by addition of a phosphate buffer solution containing 1% BSA.

After adding 100 μl of a primary reaction solution containing Triton X100, sodium dodecyl-N-sarcosinate and urea and 100 μl of the specimen in that order and stirring, the reaction was carried out at room temperature for 1.5 hours. After removing the unreacted matter by washing with a phosphate buffer solution containing a low concentration of added surfactant, a secondary reaction solution containing the anti-HCV core antigen monoclonal antibody C11-14 labeled with horseradish peroxidase and anti-human IgG mouse monoclonal antibody was added for reaction at room temperature for 30 minutes.

After completion of the reaction, the unreacted matter was removed by washing with a phosphate buffer solution containing a low concentration of added surfactant, and a substrate solution (ortho-phenylenediamine) was added for reaction at room temperature for 20 minutes, after which the luminescence was measured.

HCV antibody-positive human serum which had been confirmed to contain virtually no HCV core antigen was diluted with horse serum and used for specimens to confirm detection of antibodies for the HCV epitope, by which it was found to react in a concentration-dependent manner and the antibody was confirmed to be detected without inactivation in the primary reaction solution.

TABLE 5

Simultaneous measurement of HCV antigen and HCV antibody

| Sample | | Labeled antibody: | | |
|---|---|---|---|---|
| | | (Comp. Ex.) POD-labeled c11-14 | (Comp. Ex.) POD-labeled anti-human IgG | (Invention) POD-labeled c11-14 and POD-labeled anti-human IgG |
| | Positive | Solid phase | | |
| Recombinant core antigen ng/ml | serum dilution degree | c11-3 and c11-7 | CEPM | c11-3 and c11-7 and CEPM |
| — | — | 0.001 | 0.000 | 0.000 |
| 50 | — | 2.784 | 0.000 | 2.834 |
| 12.5 | — | 2.822 | 0.000 | 2.758 |
| 3.1 | x2048 | 1.586 | 0.210 | 1.341 |
| 0.78 | x512 | 0.423 | 0.539 | 0.815 |
| 0.2 | x128 | 0.085 | 1.139 | 1.151 |
| 0.048 | x32 | 0.014 | 1.746 | 1.621 |
| — | x8 | 0.000 | 2.161 | 1.824 |

(Values: OD492/OD690)

Separately, a recombinant core antigen was added to horse serum and diluted with horse serum for use as specimens, which were measured to confirm that the recombinant core antigen could be detected in a concentration-dependent manner.

When specimens containing appropriate amounts of added core antigen and human serum were used as specimens, a signal for the recombinant core antigen was obtained when only the recombinant core antigen was present, a signal for only the HCV antibody was obtained when only the human HCV antibody-positive serum was present, and a summated signal of both signals was obtained when both were present, as shown in Table 4. It was thus shown that both the antigen detection system and the antibody detection system functioned properly without interfering with each other, thus allowing detection of the HCV antigen and the antibody for the HCV polypeptide epitope.

Example 7

Antigen-Antibody Assay Method for Human Serum

A healthy human specimen, a patient specimen and a serum positive-conversion panel specimen (BBI, Inc.) were used for simultaneous measurement of antigen and antibody according to the method described in Example 6. The panel serum was used for comparison with the results determined using a vending agency-supplied HCV antibody detection reagent.

The results of measurement of 18 healthy human specimens are shown in Table 6, and confirm that no reaction occurred in the healthy persons. Based on the distribution for the healthy persons, the critical value between positivity and negativity was determined to be 0.1.

Positive values were exhibited for all of the HCV-positive specimens, as shown in Table 7.

However, as shown in Table 8, the points 1 to 6 for which positivity could not be determined in antibody testing of the panel sera were given positive judgments. These points were given positive judgments in the results of the Amplicor HCV test, and correspond to the window period, and therefore positivity was also confirmed with the window period specimens.

TABLE 6

| Specimen No. | Absorption |
|---|---|
| Healthy human | |
| 1 | 0.063 |
| 2 | 0.057 |
| 3 | 0.066 |
| 4 | 0.025 |
| 5 | 0.045 |
| 6 | 0.063 |
| 7 | 0.047 |
| 10 | 0.033 |
| 11 | 0.036 |
| 13 | 0.037 |
| 14 | 0.030 |
| 15 | 0.028 |
| 16 | 0.031 |
| 17 | 0.040 |
| 18 | 0.051 |
| 19 | 0.052 |
| 20 | 0.031 |
| 21 | 0.053 |
| mean | 0.044 |

TABLE 7

| Patient specimens | Absorption |
|---|---|
| 3 | 2.892 positive |
| 16 | 2.335 positive |
| 45 | 0.394 positive |
| 84 | 2.769 positive |

TABLE 8

| Panel sera | Absorption | Judgment | Antibody assay | Amplicor HCV test |
|---|---|---|---|---|
| PHV907-1 | 0.557 | positive | negative | positive |
| 2 | 0.397 | positive | negative | positive |
| 3 | 0.357 | positive | negative | positive |

TABLE 8-continued

| Panel sera | Absorption | Judgment | Antibody assay | Amplicor HCV test |
|---|---|---|---|---|
| 4 | 0.224 | positive | negative | positive |
| 5 | 0.192 | positive | negative | positive |
| 6 | 0.247 | positive | positive | positive |
| 7 | 2.414 | positive | positive | positive |

Example 8

Preparation of Monoclonal Antibody

According to the method described in Example 3, another hybridoma was constructed and designated as HC11-15. This hybridoma was deposited at the National Institute of Bioscience and Human Technology on Jul. 16, 1999 as FERM BP-9782. Monoclonal antibody produced by this hybridoma was purified and its isotype was identified as IgG1. As a result of an epitope analysis using 20 peptides synthesized on the basis of the sequence of core region, said monoclonal antibody was found to specifically recognize $^{15}$Thr-$^{30}$Ile (SEQ ID NO:9).

Example 9

Determination of Antibody Titer of the Monoclonal Antibody

The recombinant core antigen (Trp C11) was diluted in 10 mM phosphate buffer (pH 7.3) containing 6M urea to a final concentration of 2 μg/ml, and 100 μl of the solution was added to each well of a microplate. After allowing to stand at 4° C. overnight, the solution was aspirated off, and the wells were washed twice with 10 mM phosphate buffer (pH 7.3). 350 μl of 10 mM phosphate buffer (pH 7.3) containing 0.5% casein was added to each well, and after incubation at room temperature for an hour, the buffer was aspirated off. Each monoclonal antibody (C11-3, C11-7, C11-10, C11-14 or C11-15) sequentially diluted with a reaction mixture was added to each well, and reacted for an hour. After washing, a peroxidase-labeled anti-mouse antibody was added, reacted for 30 minutes, and after washing, an enzyme reaction was carried out by adding a substrate solution comprising orthophenylenediamine and hydrogen peroxide. After reaction at room temperature for 30 minutes, 2N sulfuric acid was added to terminate the enzyme reaction, and absorbance at 492 nm was measured by a microplate reader.

The C11-15 exhibited the highest antibody titer, revealing that if this antibody is used as a secondary antigen, detection with a high sensitivity can be obtained.

Example 10

Sandwich ELISA Using Different Immobilized Monoclonal Antibodies

Figure 1:
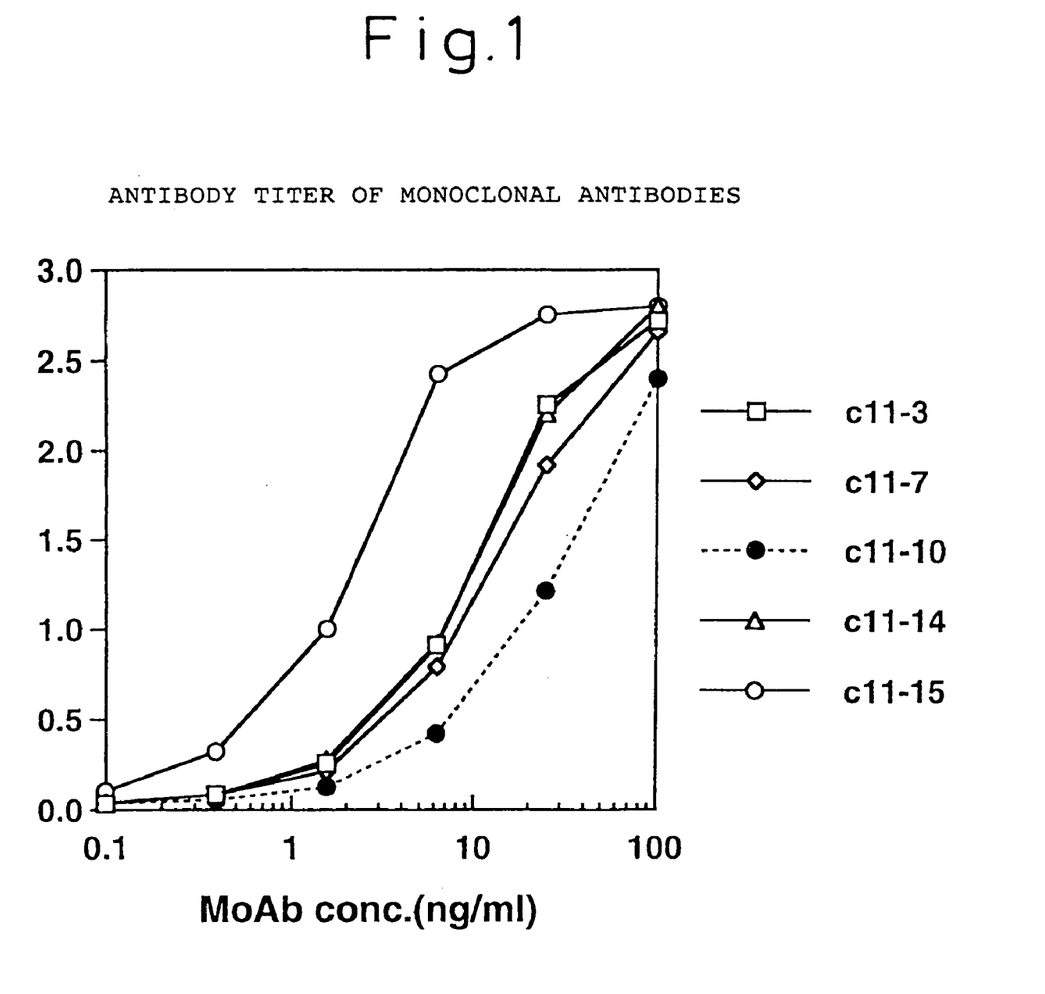
FIG. 1 is a graph showing a comparison of antibody titer of monoclonal antibody C11-15 with antibody titers of other monoclonal antibodies C11-3, C11-7, C11-10 and C11-14.
Figure 2:
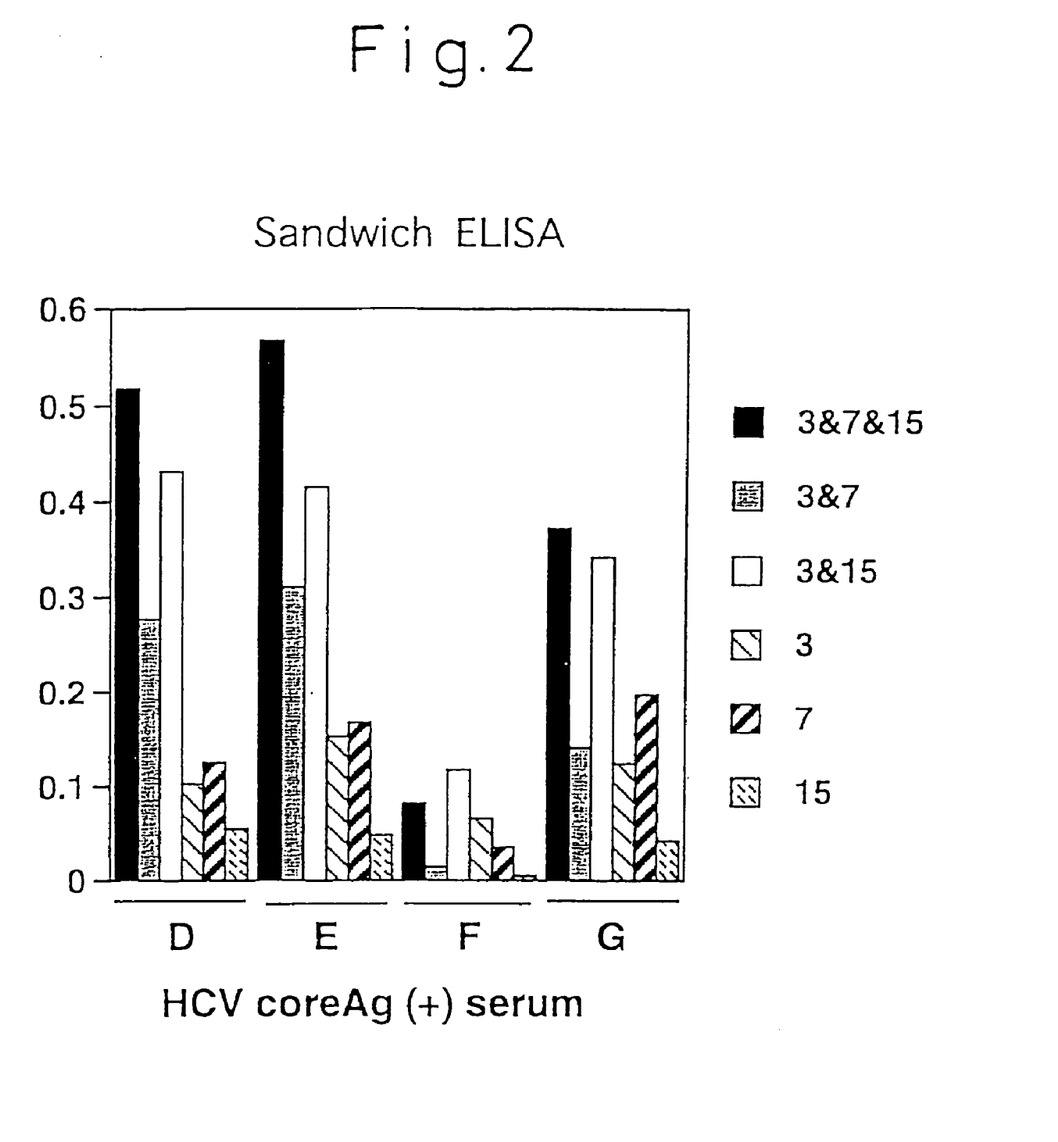
FIG. 2 is a graph showing a result of ELISA for measuring HCV-RNA positive specimen using as primary antigen immobilized on a solid phase each of various monoclonal antibodies alone, or mixture thereof.

Monoclonal antibody (C11-3, C11-5, and C11-15; C11-3 and C11-7; C11-3 and C11-15; C11-3 alone; C11-7 alone; or C11-15 alone) was diluted in 10 mM phosphate buffer (pH 7.3) to a final concentration of 6 μg/ml, and 100 μl of the solution was added to each well of microplate. After allowing to stand at 4° C. overnight, the buffer was aspirated off, and the wells were washed twice with 10 mM phosphate buffer (pH 7.3). 350 μl of 10 mM phosphate buffer (pH 7.3) containing 0.5% casein was added, and after incubation at room temperature for two hours, the buffer was aspirated off. 100 μl of a specimen which is HCV-RNA positive and anti-HCV antibody negative and 100 μl of a reaction solution were added to each well, and reacted at room temperature for an hour. After washing, a peroxidase-labeled anti-core antigen monoclonal antibody (a mixture of C11-14 and C11-10) was added, and reacted for 30 minutes, and after washing, an enzyme reaction was carried out by adding a substrate solution comprising orthophenylenediamine and hydrogen peroxide. After reaction at room temperature for 30 minutes, 2N sulfuric acid was added to terminate the enzyme reaction, and the absorvance at 292 nm was measured by a microplate reader. A result is shown in FIG. 2.

It was revealed that although detection sensitivity is low if only C11-15 was immobilized, the detection sensitivity increases by monobilizing a mixture of C11-15, and C11-3 or C11-7 etc.

Example 11

Expression and Purification of Epitope-Chimeric Antigen

E. coli transformant CEPM/HB101 was cultured in an LB medium containing 100 μg/ml ampicillin at 37° C. overnight. The culture was inoculated to M9-CA containing 100 μg/ml ampicillin by an inoculum size of 1% concentration, and cultured at 37° C. overnight. After finishing the culturing, the microbial cells were collected by centrifugation, and resuspended in 50 ml of a lysis solution [50 mM Tris-HCl (pH 8.5), 30 mM NaCl, 5 mM EDTA), and after adding 1 ml of a lysozyme solution (10 mg/ml Lysozyme), were inoculated at 37° C. for an hour. This suspension was subjected to ultrasonication (150 W, 90 seconds, twice) so as to disrupt the cells. An insoluble fraction was recovered by centrifugation at 15000 rpm, 4° C. for 30 minutes. The insoluble fraction was resuspended in 50 ml of A solution [50 mM Tris-HCl (pH 8.5)] containing 1% NP40, and homogenated (1500 rpm, 5 strokes). The suspension was centrifuged at 1500 rpm, 4° C. for 30 minutes to recover an insoluble fraction. The insoluble fraction was resuspended in 50 ml of the A solution containing 2M urea, and homogenized (1500 rpm, 5 strokes). The suspension was centrifuged at 15000 rpm, 4° C. for 30 minutes to recover an insoluble fraction. The insoluble fraction was resuspended in 50 ml of the solution A containing 6M urea, and homogenized (1500 rpm, 5 strokes). The suspension was centrifuged at 15000 rpm, 4° C. for 30 minutes to recover a soluble fraction.

The epitope chimeric antigen was purified from the antigen solution prepared by solubilization with 6M urea-containing solution, by an ion exchange using S Sepharose HP column (Pharmacia) and gel-filtration using Superdex 75 pg (Pharmacia).

Note that an nucleotide sequence of DNA encoding said chimeric antigen is shown in SEQ ID NO:10, and the amino acid sequence of the chimeric antigen is shown in SEQ ID NO:11.

Reference to Microorganisms Deposited Under Rule 13-2 of PCT and Depository Institute Depository Institute
　Name: The National Institute of Bioscience and Human Technology
　Address: 1-3, Higashi 1-chome, Tsukuba-shi, Ibaraki, Japan Microorganisms
 (1) Identification: HC11-3
  Deposition No: FERM BP-6002
  Deposition date: Jul. 4, 1997
 (2) Identification: HC11-7
  Deposition No: FERM BP-6003
  Deposition date: Jul. 4, 1997
 (3) Identification: HC11-10
  Deposition No: FERM BP-6004
  Deposition date: Jul. 4, 1997
 (4) Identification: HC11-11
  Deposition No: FERM BP-6005
  Deposition date: Jul. 4, 1997
 (5) Identification: HC11-4
  Deposition No: FERM BP-6006
  Deposition date: Jul. 4, 1997
 (6) Identification: HC11-15
  Deposition No: FERM BP-6782
  Deposition date: Jul. 16, 1999

The invention claimed is:

1. A method for determining the presence of Hepatitis C virus (HCV) core antigen and anti-HCV core antibodies in a sample, at the same time, in the same vessel, using (1) antibodies for the detection of HCV core antigen and (2) at least one peptide for the detection of core antibodies wherein at least one peptide lacks epitopes recognized by said antibodies for detection of HCV core antigen, comprising the steps of:
   (a) contacting the sample (1) with an antibody or antibodies for detection of HCV core antigen and (2) with the at least one peptide for detection of the anti-HCV core antibodies, and
   (b) detecting (1) the HCV core antigen by an antibody or antibodies for detection of the HCV core antigen, and (2) the anti-HCV core antibodies;

wherein said antibodies for detection of HCV core antigen are selected from antibodies recognizing and binding to a region from position 100 to 130 or from position 41 to 50 of HCV core antigen,
   wherein said sample is contacted with said antibodies for detection of HCV core antigen and said at least one peptide in the presence of one or more detergents with one or more alkyl chains having 12 to 16 carbon and one or more tertiary or quaternary amines, or one or more non-ionic surfactants with an HLB value of 12 to 14 and a concentration of 0.5% or greater.

2. The method according to claim 1, wherein said antibodies for detection of HCV core antigen are antibodies recognizing and binding to a region from position 100 to position 130 of HCV core antigen.

* * * * *